(12) United States Patent
Taylor et al.

(10) Patent No.: US 8,529,437 B2
(45) Date of Patent: Sep. 10, 2013

(54) MULTIFUNCTIONAL SURGICAL INSTRUMENT WITH FLEXIBLE END EFFECTOR TOOLS

(75) Inventors: Warren Taylor, Longmont, CO (US); Brian Jackman, Milwaukee, WI (US); David Newton, Longmont, CO (US); Gary Broeder, Erie, CO (US)

(73) Assignee: Encision, Inc., Boulder, CO (US)

( * ) Notice: Subject to any disclaimer, the term of this patent is extended or adjusted under 35 U.S.C. 154(b) by 798 days.

(21) Appl. No.: 12/536,364

(22) Filed: Aug. 5, 2009

(65) Prior Publication Data

US 2010/0036380 A1    Feb. 11, 2010

Related U.S. Application Data

(60) Provisional application No. 61/086,602, filed on Aug. 6, 2008.

(51) Int. Cl.
*A61B 1/00* (2006.01)

(52) U.S. Cl.
USPC .......................................... 600/141; 606/207

(58) Field of Classification Search
USPC .............. 606/50–52, 205–207; 600/139–144
See application file for complete search history.

(56) References Cited

U.S. PATENT DOCUMENTS

| 5,904,647 A * | 5/1999 | Ouchi ........................... 600/104 |
| 2001/0021861 A1 * | 9/2001 | Boebel et al. ................. 606/207 |
| 2005/0137585 A1 | 6/2005 | Landman et al. |
| 2006/0178564 A1 | 8/2006 | Jones et al. |
| 2007/0135803 A1 | 6/2007 | Belson |
| 2007/0179525 A1 | 8/2007 | Frecker et al. |
| 2007/0250113 A1 * | 10/2007 | Hegeman et al. ............. 606/207 |
| 2009/0088792 A1 * | 4/2009 | Hoell et al. ................... 606/206 |

OTHER PUBLICATIONS

Baharlou, Simin, "PCT International Report on Patentability re Patent Application PCT/US09/052961", Feb. 17, 2011, Published in: CH.
Young, Lee W., "PCT International Search Report re Application No. PCT/US09/52961" dated Nov. 5, 2009.

* cited by examiner

*Primary Examiner* — Michael Peffley
(74) *Attorney, Agent, or Firm* — Neugeboren O'Dowd PC

(57) ABSTRACT

A surgical tool having proximal and distal ends and adapted to transverse a curved passageway comprises an end effector disposed on the distal end of the surgical tool, the end effector having a first body section and a second body section and a releasable connector joining the end effector first body section with the end effector second body section. The connector is operable to reversibly engage the first and second end effector body sections in a first fixed position and in a second movable position. The surgical tool further comprises an actuation device for moving the first and second end effector body sections from the first fixed position to the second movable position. The end effector is adapted to maneuver through a larger radius of curvature in the second movable position than in the first fixed position.

11 Claims, 14 Drawing Sheets

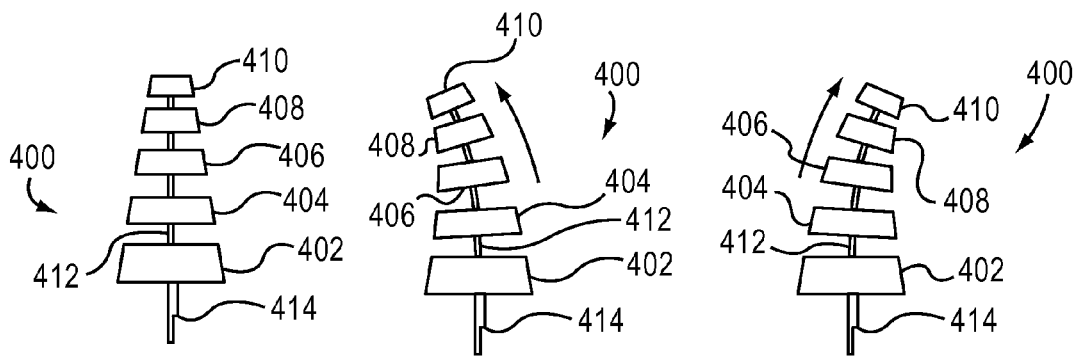
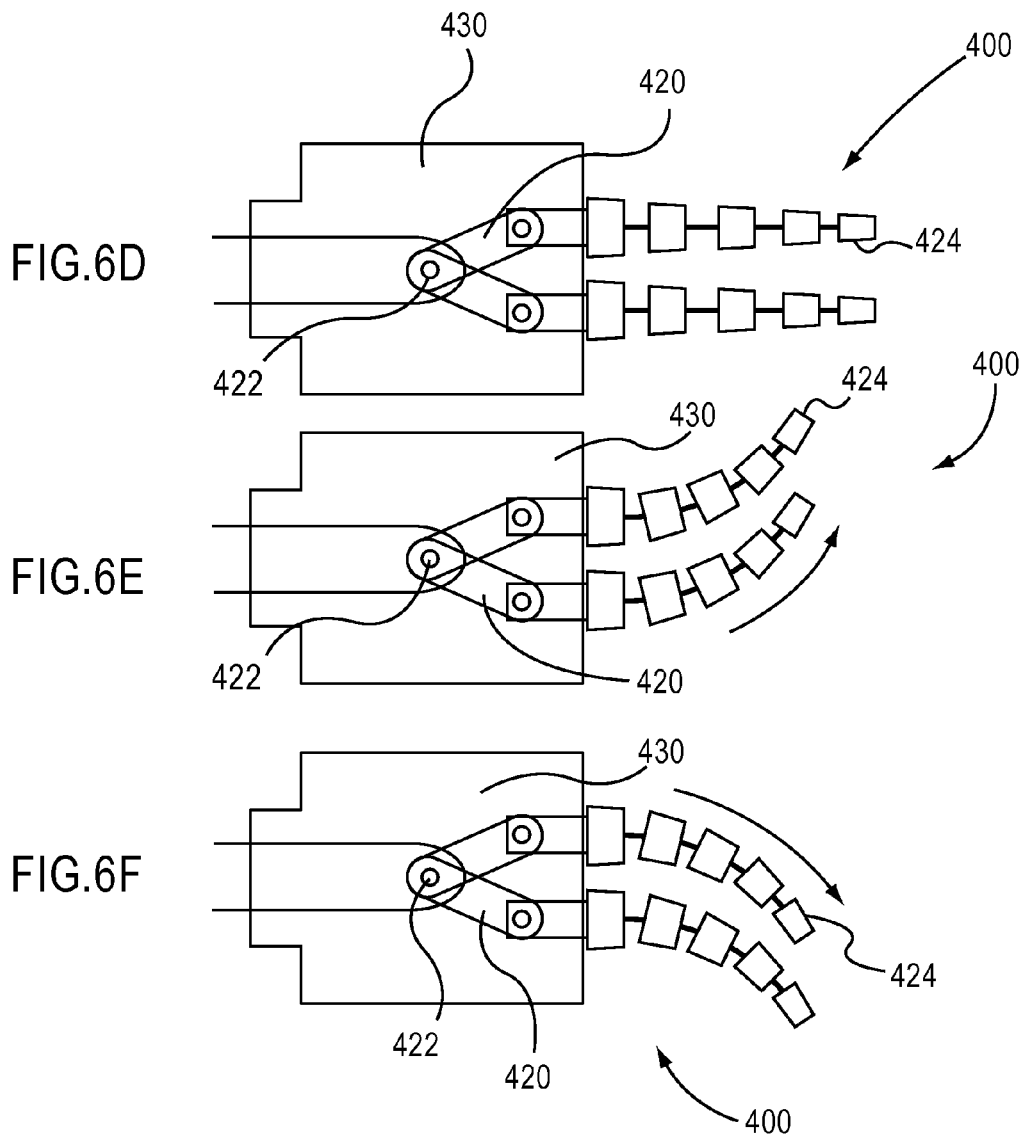

MULTIFUNCTIONAL SURGICAL INSTRUMENT WITH FLEXIBLE END EFFECTOR TOOLS

PRIORITY AND RELATED APPLICATIONS

This application claims the benefit of Provisional U.S. Application No. 61/086,602 filed on Aug. 6, 2008. The details of Application No. 61/086,602 are incorporated by reference into the present application in its entirety and for all proper purposes.

FIELD OF THE INVENTION

Aspects of the present invention relate to surgical instruments adapted for use in minimally invasive/laparoscopic surgical procedures. In particular, but not by way of limitation, aspects of devices constructed in accordance with the present invention relate to multifunctional end effectors for attachment to and use with laparoscopic surgical instruments such as flexible surgical instrument assemblies and surgical instrument assemblies used in connection with complex tools, such as robotics and other enhanced control devices, sometimes referred to as enhanced control devices. Other aspects relate to end effectors that are designed to travel through flexible lumens or other passages either in traditional surgical tools or in surgical tools used with enhanced control devices.

BACKGROUND

Modern surgical procedures are increasingly utilizing complex surgical tools such as robots, computer assisted instruments, multifunctional instruments, and other devices that utilize enhanced control systems (ECS). Enhanced control systems are systems that consist of mechanical or electromechanical configurations and that may provide one or more endo-mechanical features that provide a surgeon with improved surgical end effector mobility. Examples of improvements include increased instrument flexibility, better ergonomic positioning, hand tremor reduction, translation of motion frames of reference, telesurgery, including robotic systems and the like. ECS typically involves more elaborate instruments and support structures for the instruments compared to typical laparoscopic surgery and may also include the use of novel body entry devices and different points of entry compared to laparoscopic or other minimally invasive surgical techniques. Many of these enhanced control devices utilize in some form a flexible endoscope as the primary method for accessing areas of the body. Flexible endoscopes typically have a primary channel where a camera is located along with lighting fibers. The endoscopes also have additional channels (also called operating or working lumens) for transversing instruments through the endoscope and emerging out at the end of the endoscope proximate to the surgical site. One or more of the instruments can then be utilized or otherwise controlled for surgical tissue applications.

In systems that utilize an endoscope or other flexible device, the scope itself is flexible and thus the lumens that are contained within the scope for the insertion of instruments, are also flexible. The scopes are generally manipulated into a position where the camera can view the area of interest. The scope can then be "locked" into this position (if the design permits) or simply held. Auxiliary instruments are then guided down the operating lumens while the scope is held in position. Since the scope is bent and/or otherwise curved in varying angles, the internal lumens are also bent. Therefore, as an instrument is inserted down the working lumen, any rigid parts of the instrument must pass through the radius/radii of the bent lumen. Therefore, the radii of any bends in the lumen necessarily limit the length of the inserted instrument. The diameter of the lumen itself also limits the size of the instrument. For example, the length and size of a jaw and instrument housing may be limited. In some cases the endoscope can be straightened when exchanging instruments allowing for longer instrument jaws to be inserted, but this is not desirable since the field of interest will have to be re-established once the instrument is through the lumen. Locating the endoscope back into the previous position can be very time consuming and dangerous.

Since the jaws of the instruments used for these procedures, which can include single orifice procedures, scar-less procedures, and single port of entry procedures, are limited in length, the function of the associated end effectors may be compromised. For example, a grasper inserted into a lumen of this type cannot manipulate as much tissue as other graspers since the jaw length will be much shorter (to accommodate passing through the curved sections of the lumen) than the grasper jaw length normally used in a minimally invasive surgical procedure. In order to achieve a longer, more conventional jaw length while still allowing the instrument to transverse down a flexible scope's working lumen, the jaws and other end effectors used with these surgical instruments need to be modified.

In addition, incorporating a multi-function end effector into a single instrument will eliminate or at least decrease the requirement that one instrument be removed and exchanged for a second instrument when a second instrument is needed during a minimally invasive procedure and can also serve to reduce the dimensional profile of the end effector, allowing easier passage through a curved lumen. Eliminating or substantially decreasing instrument exchange may save valuable time during a surgical procedure, allowing a health professional to perform other critical functions.

What is needed is a surgical tool that can accommodate an end effector having multiple functions and that can transverse or otherwise pass through a flexible lumen.

SUMMARY OF THE INVENTION

In accordance with one aspect, a surgical tool comprises an end effector disposed on the distal end of the surgical tool, the end effector having a first body section and a second body section, and a connector joining the end effector first body section with the end effector second body section. The connector is operable to engage the first and second end effector body sections in a first fixed position and in a second movable position.

In one embodiment, the surgical tool further comprises an actuation device for moving the first and second end effector body sections from the first fixed position to the second movable position. In another embodiment, the end effector is adapted to maneuver through a larger radius of curvature in the second movable position than in the first fixed position.

Other aspect will become apparent to one of skill in the art upon a review of the following drawings and detailed description.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings, wherein:

FIGS. 6A-8B show yet another embodiment of a flexible end effector in accordance with aspects of the present invention;

FIGS. 15A-16B show an embodiment of a sliding jaw end effector in accordance with aspects of the present invention;

DETAILED DESCRIPTION

In accordance with one aspect, an end effector such as a grasper jaw is adapted to provide a larger working area while also being able to pass through the radii of a curved or flexible working lumen. In this aspect the end effector is designed to include a series of segments adapted to remain substantially rigid in a first position and to articulate, bend or otherwise flex when in a second position. In general terms, the end effector is comprised of two conventional opposing jaws, each jaw comprised of several jaw segments or sections. Each jaw section may be joined by a connector such as a pin, pivot or hinge that allows the sections to rotate around a curve of the working lumen when in its flexible orientation. As an analogy, the jaw sections operate similar to train cars going around a bend in the tracks. Once the jaw transverses the working lumen and emerges in the body cavity, the jaws can then be locked together to act as a single larger jaw. As described in more detail below, the locking mechanism can have several variations. To remove the jaw through the flexible lumen, the jaw sections are unlocked and allowed to pivot in order to enable the end effector to exit the working lumen.

Figure 1A:
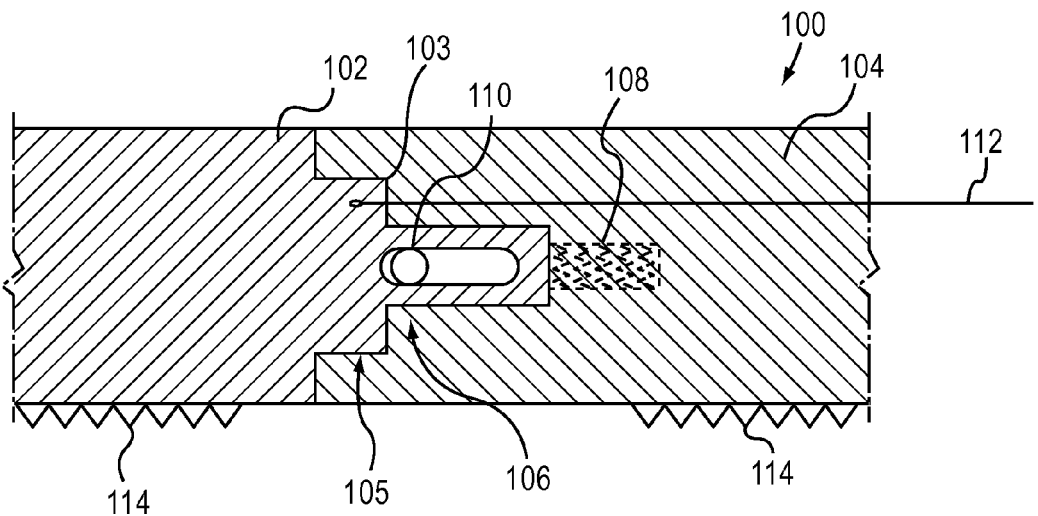
FIGS. 1A-1C show one embodiment of a flexible end effector in accordance with aspects of the present invention.
Figure 1B:
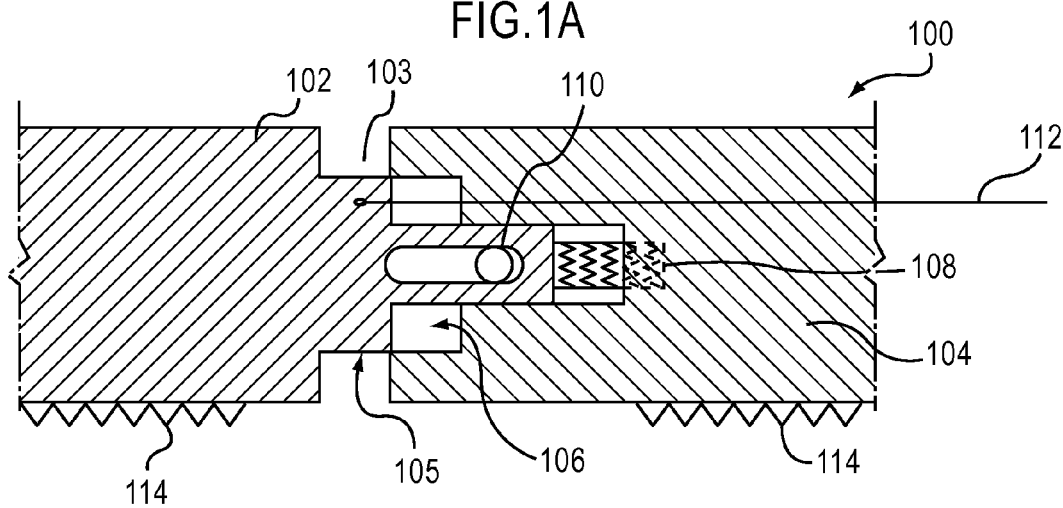
Figure 1C:
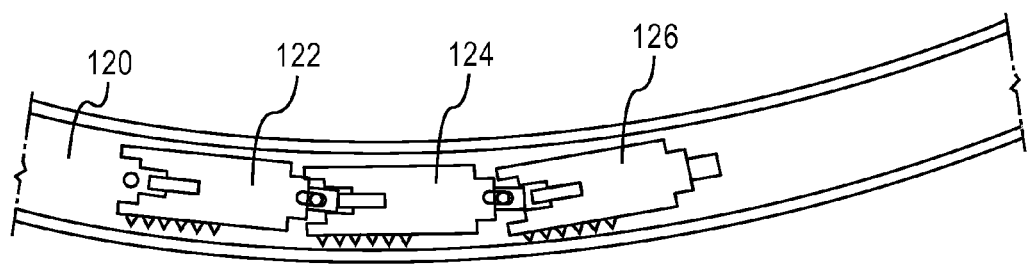

FIGS. 1A-1C show a representative example of such a "train jaw" embodiment (a working embodiment would comprise two opposing jaws). With reference to FIG. 1A a cross section of a train jaw 100 including two jaw sections 102 and 104 is shown. Section 102 includes a stepped portion 103 that is designed to snugly interface with stepped portion 105 of jaw section 104. The stepped portions 103 and 105 are designed to mate with each other so that a substantially uniform and rigid component is formed between sections 102 and 104 when the sections are engaged. A pin, hinge, pivot or other connector 110 is disposed between the sections 102 and 104 and prevents the sections 102 and 104 from becoming disengaged with each other when the jaw is in its unlocked or flexible position. The connector 110 also provides the necessary rotation between sections 102 and 104 and enables the sections to flex when traveling through a lumen. In another embodiment, a connector such as a universal joint can flex or pivot in three dimensions. A spring biasing element 108 is disposed at the interface of sections 102 and 104 and allows an actuation wire 112 to pull the sections 102 and 104 into a locked position. Releasing the tension on actuation wire 108 biases the sections 102 and 104 into an unlocked position allowing them to rotate or otherwise flex around connector 110. Each of the jaw sections 102 and 104 include surfaces 114 that provide the end effector with its functionality. In the example shown in FIGS. 1A-1C, the surfaces 114 are shown as grasping surfaces, consistent with the example of an end effector grasper device. A mirror image of the jaw assembly sections 102 and 104 can also be assembled with opposing teeth or surfaces 114 to provide grasping function like existing laparoscopic instruments.

FIG. 1B shows the same device as FIG. 1A except in the unlocked position that allows the sections 102 and 104 to swivel, pivot, rotate or otherwise flex when transversing a curved lumen. Depending on the desired action of the sections 102 and 104, the connector 110 can be modified or selected to provide various types of movement and degrees of freedom between the sections 102 and 104.

FIG. 1C shows a series of three jaw sections 122, 124, and 126 connected and engaged with each other in the flexible position and while transversing the length of a curved lumen 120. In operation, the sections 122, 124 and 126 remain in the flexible position while traveling through the lumen. After exiting the lumen proximate to a surgical site, the actuation wire is pulled or otherwise activated, the jaw sections are joined and the three sections remain in a rigid configuration for use as a grasper or other end effector.

As mentioned above, various methods and structures can be utilized to engage and disengage the several jaw sections while also allowing them to pivot or flex through a curved passageway. As described above, an actuation wire 112 can be utilized. The wire is pulled to lock the jaws and released to allow a biasing spring 108 to push the jaws apart.

Figure 2:
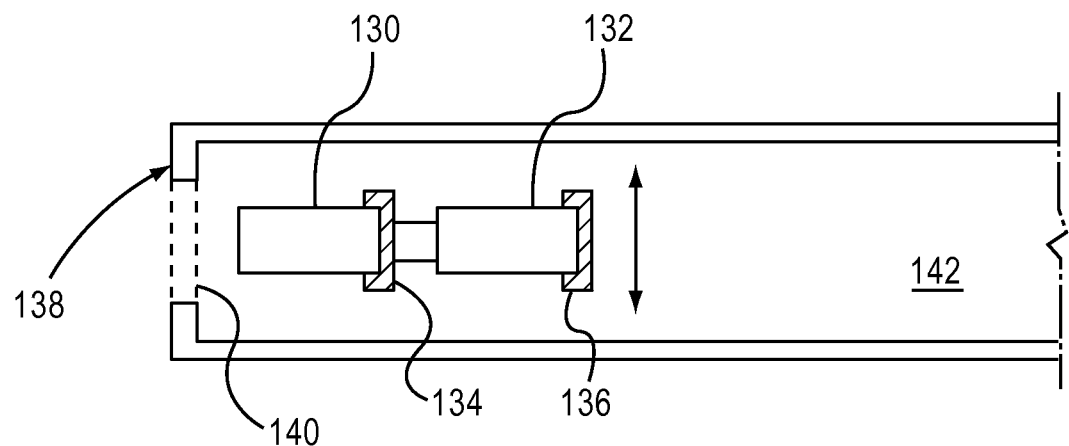
FIG. 2 shows another embodiment of a flexible end effector in accordance with aspects of the present invention.

In FIG. 2 a toggle embodiment is shown as the mechanism to engage and disengage the jaw sections. Two jaw sections 130 and 132 are shown each with a pin 134 and 136 extending out the side of the jaw. As the jaw is pushed through the distal end 138 of a lumen 142, an orifice 140 on the distal end 138, which is just smaller than the outer diameter of the jaw pins interacts with the jaw pins and causes the jaw pins to toggle into a position that locks the two jaws 130 and 132 together. As each jaw exits the lumen it is locked with the next jaw. When the jaws are retracted back into the lumen 142, the orifice 140 causes the pins to rotate back into the unlock position allowing the jaws to become rotatable again.

Figure 3:
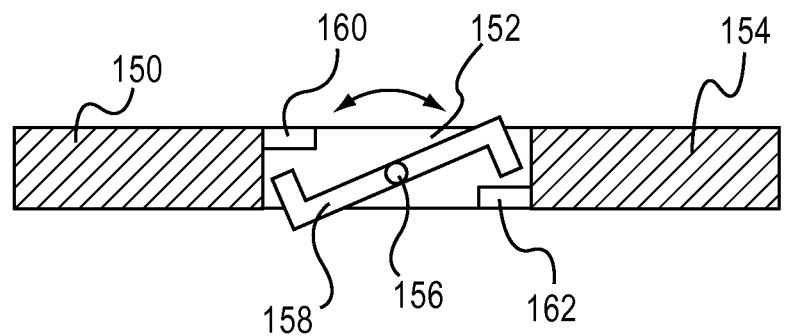
FIG. 3 shows yet another embodiment of a flexible end effector in accordance with aspects of the present invention.

In FIG. 3, a manual lock assist embodiment is shown as the mechanism to engage and disengage the jaw sections. Because end effector tools are normally used in tandem with other instruments, in this embodiment the jaws may be locked together by using another instrument to toggle or "flip" a locking plate. In FIG. 3, jaw sections 150, 152 and 154 are connected together by a rotatable hinge. Disposed alongside or within one or more of the jaw sections is a locking plate 158 that can rotate about a pin 156 into and out of engagement with portions 160 and 162 of the jaw section. Another instrument inside the patient can be maneuvered to rotate the locking plate 158 to engage the jaw sections on either side to lock jaws together.

Variations on the above embodiments can also be utilized to engage and disengage the jaw sections. For example, the orifice plate in FIG. 2 could be constructed to also rotate the plate as the jaws leave the orifice. The same structure could be used to "unrotate" the plate when the jaw is retracted.

Figure 4A:
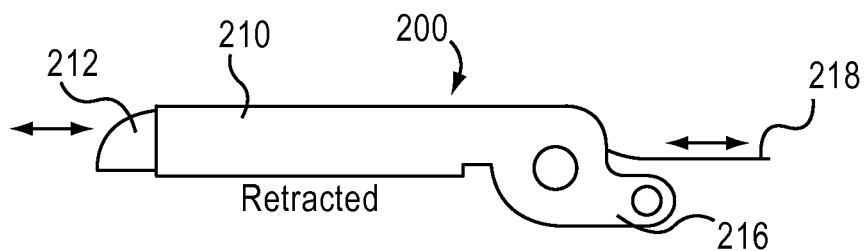
FIGS. 4A-4C show an embodiment of a telescoping end effector in accordance with aspects of the present invention.
Figure 4B:
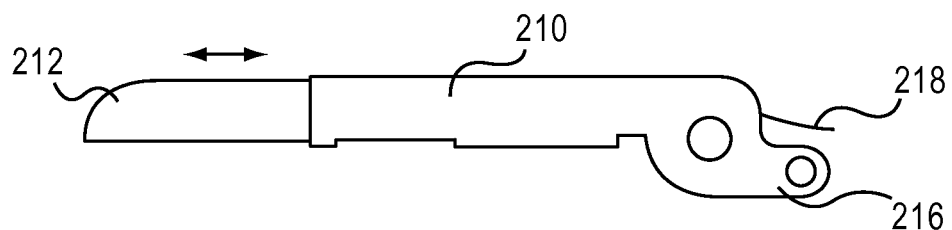
Figure 4C:
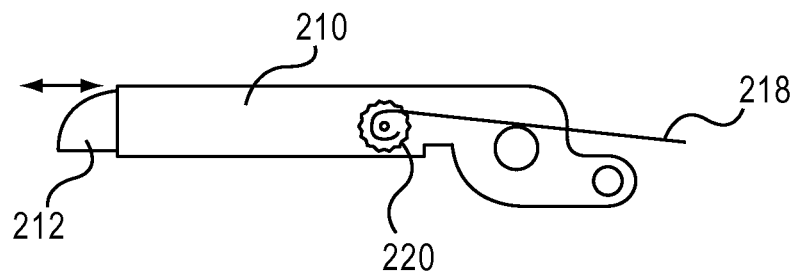

With reference to FIGS. 4A through 4C, another embodiment of an end effector constructed in accordance with aspects of the present invention is shown. In this embodiment, a jaw 200 is comprised of at least two telescoping sections 210 and 212 that can be moved in an in/out manner through an actuation mechanism. The sections 210 and 212 can each be manipulated to an extended position once through the working lumen. The extension of the jaw sections can be accomplished via a push/pull wire (shown in FIG. 4A as reference number 218), a rack and pinion section (shown in FIG. 4C as reference number 220), or manipulated into an extended position by using another grasper that is located inside the patient during a surgical procedure. A spring biasing member (not shown in the Figures) may also be incorporated into the end effector to enable the telescoping portions to be extended and retracted. A mounting section 216 may be incorporated into the end effector and connected to a delivery mechanism capable of also transversing a flexible lumen.

Figure 5A:
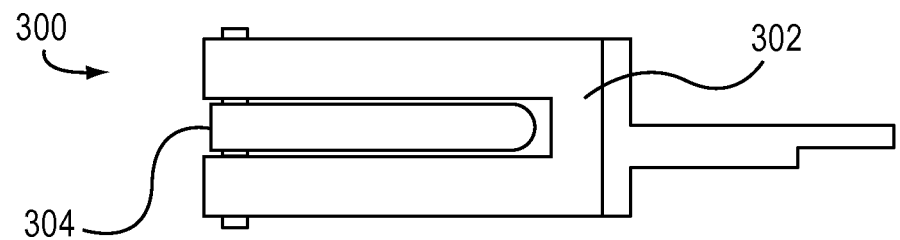
FIGS. 5A-5B show an embodiment of a folding end effector in accordance with aspects of the present invention.
Figure 5B:
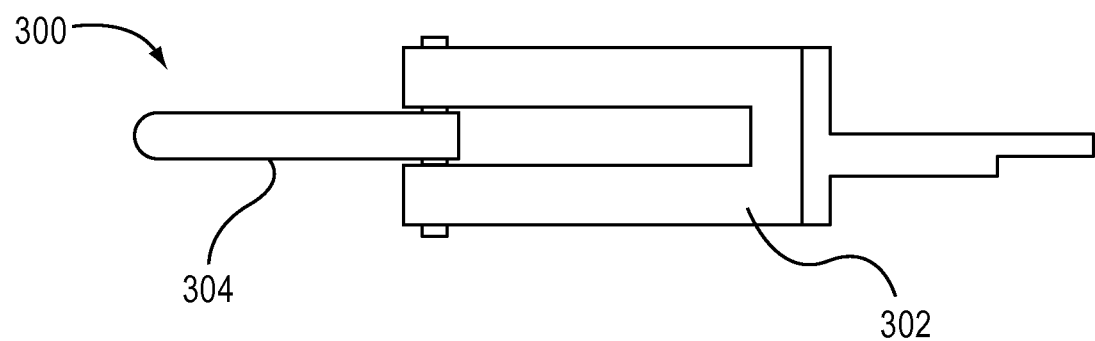

With reference to FIGS. 5A and 5B, another embodiment of an end effector constructed in accordance with aspects of the present invention is comprised of a jaw adapted to fold and unfold in order to better transverse a curved lumen. While similar in function to the telescoping jaw embodiment discussed above in that the overall size of the end effector is reduced in one position to allow it to transverse a flexible or otherwise curved lumen, this fold/unfold jaw embodiment utilizes one or more jaw sections that can be unfolded into an extended position. With reference to FIG. 5A an end effector 300 generally includes a first body portion 302 and a second body portion 304. Portion 304 is adapted to fold into a slot within portion 302 such that the overall length of the end effector is smaller when the device is in its folded position. FIG. 5B shows the end effector in its folded position. Several methods can be used for folding and unfolding the jaws including actuation wires or by user assist (e.g. using another instrument already located inside the patient to unfold the jaws).

Another embodiment of an end effector adapted to navigate narrow lumen radii while still providing the functionality of larger jaws is described with reference to FIGS. 6A-6F. In general, an end effector such as a grasper jaw includes a plurality of horizontal sections that can be manipulated into a flexible position. The jaw is formed from a series of individual pieces which are themselves very rigid while the assembly of jaw pieces can flex or change shape with relation to each other. A linkage disposed between and interconnecting the jaw pieces is such that freedom of movement is allowed in one or more directions. FIGS. 6A-6C show a top down view of an end effector 400, in this example shown as a grasper jaw, that includes five sections 402, 404, 406, 408 and 410. A linkage 412 such as a wire formed from a resilient material such as Nitinol passes through each of the sections 402-410. The linkage serves to interconnect the sections and also allows the entire end effector 400 to bend and/or flex in one or more directions. FIGS. 6B and 6C illustrate how the end effector can bend left and right. A mounting section 414 on the proximal end of the end effector 400 allows the tool to be connected to the operable end of a larger surgical tool such as a grasper assembly. FIGS. 6D-6F show side views of the end effector 400 in a neutral position (FIG. 6D) flexed upward (FIG. 6E) and flexed downward (FIG. 6F). The end effector 400 is also shown attached to a linkage 420 and pivot 422 that provides the grasping motion associated with a tool such as a scissor or grasper. In practice, the end effector is inserted through a lumen 430 in order to place it at a surgical site. By combining these two ranges of motion shown in FIGS. 6A-6F, a combination of up/down, left/right movements is achieved and a variety of unique positions in 2D and/or 3D space are created.

Figure 7:
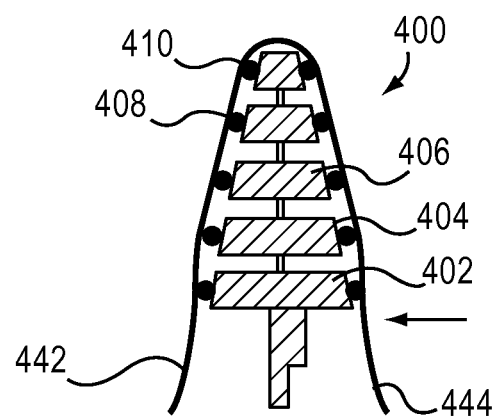
Figure 8A:
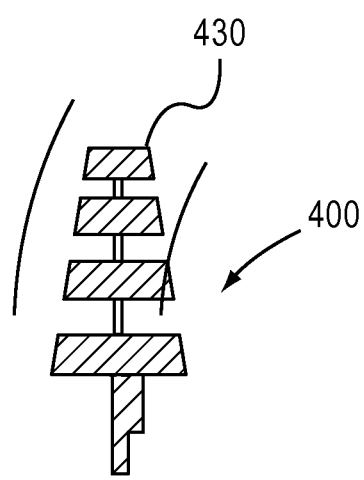
Figure 8B:
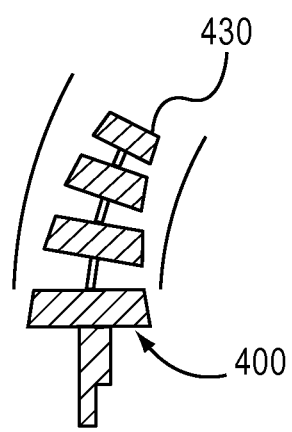

With reference to FIG. 7, a first embodiment showing how the motion of this device can be controlled is shown. One or more guide wires 440 and 442 are disposed on the outside of the end effector sections 402-410. When activated and placed in tension or traction, the guide wires 442 and 444 create various tensions on the jaw enabling it to form one or more of the shapes described in FIGS. 6A-6F. As such a user can maneuver the end effector through a lumen that is curved. A guide wire may also be disposed through the middle of the end effector components rather than along the sides. FIGS. 8A and 8B illustrate how this steerable embodiment can be made to more easily transverse a lumen that contains one or more curved sections. In FIG. 8A, a rigid end effector would have difficulty maneuvering through a curved lumen section 430 while in FIG. 8B, a user can flex the end effector to more closely mimic the curves of the lumen.

In the foregoing embodiment, an end effector is created that is rigid when tension is applied to the guide wires, but limp or otherwise flexible when the tension is removed. This allows for an end effector to be passively re-shaped to fit into areas where its geometry would not previously allow it to. A larger diameter grasper then fits into a smaller cannula. For example, if one wanted to fit a jaw that had a large bend to it into the smallest possible opening, the tension is released and the jaw goes limp thus allowing the jaw to straighten for fitting through the cannula. Once through, the tension is reapplied and the jaw reforms its original shape.

In another embodiment an end effector assembly that is capable of "floating" is provided. In this embodiment, the jaws are capable of moving out of axis alignment with the housing so that the end effector assembly can be inserted around curves in the endoscope channel.

Figure 9:
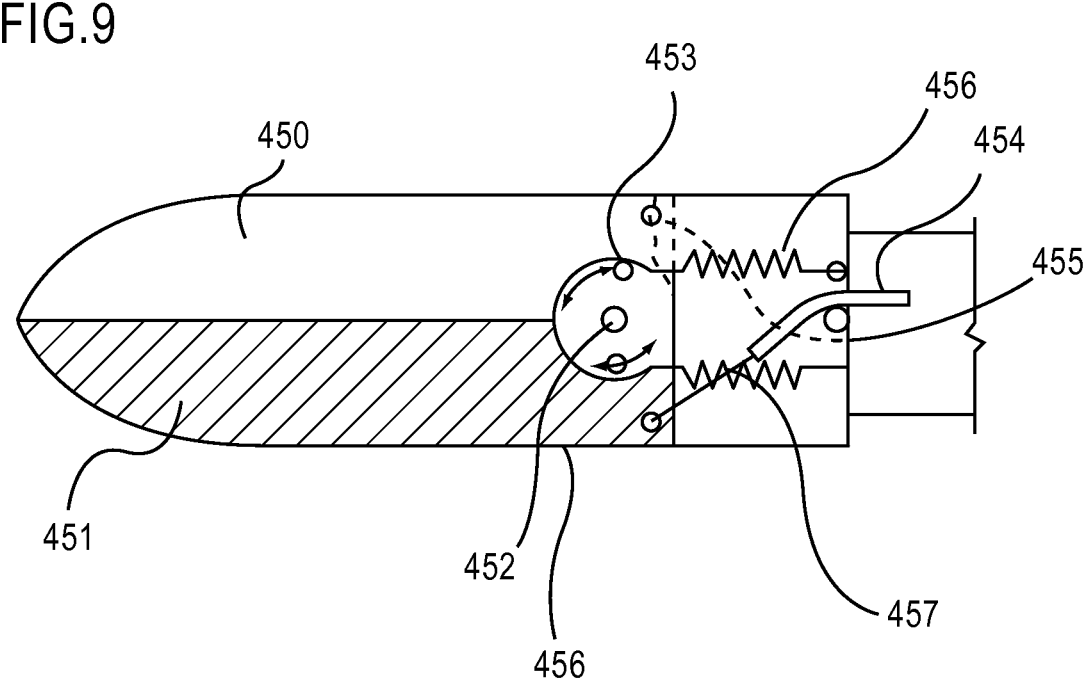
FIG. 9 shows another embodiment of a flexible end effector utilizing a floating housing in accordance with aspects of the present invention.

Conventional end effectors and housings comprise an instrument tip assembly in which the axis of the closed end effectors is always in-line with the axis of the housing. In accordance with the present embodiment, there is a "free state" defined in which an end effector is allowed to float within approximately 15-45 degrees of the axis of the housing. There is still a locked state in which the tip assembly functions normally. This free state may be used for introduction into an endoscope channel or maneuvering through a curved portion of a lumen. The locked state is used for normal grasping or cutting procedures. FIG. 9 shows one embodiment of such a floating instrument housing.

With reference to FIG. 9, jaws 450 and 451 can rotate independently around a central pivot 452. Pins or cam followers 453 and 456 confine the jaw rotation around the central pivot pin 452. Two independent Bowden type cables 454 and 455 are attached to the respective jaws. As the cables 454 and 455 are pulled or relaxed, the jaws 450 and 451 can be rotated out of plane around the central pivot pin 452. To open or close the jaws once in a rotated position, the cables 455 and 454 tension can be adjusted. Spring return or bias 456 and 457 provide the return force.

Transition between the two states would be made through a control means such as a rotation of a pull-wire, higher than normal tension on a pull-wire (a pull-pull toggle action), or action of a second pull-wire or other member.

In another embodiment, two wires may operate separately on opposing jaws such that with little or no force applied and with the pull wires floating, the jaws would also float angularly. Tension on both wires would force the jaws to close against each other. There can be a light opening spring force built into each of the tips at a magnitude that would be balanced by a slight pull-wire tension and not interfere with ability of the jaws to float and negotiate curves in a lumen channel. In addition the pull-wires can be designed with some ability to push, thus adding to the opening force. With differential movement of the pull wires the jaws could be made to close off the axis. This could be advantage particularly in endoscope systems where the angular separation of instrument approaches to tissue is limited.

In this embodiment, for instrument introduction, the tip assembly needs to be rotated so that the floating plane of the tips line up with the planes of curvature of the channel of the system. An enhancement may be possible in which the housing sides angle outward in the free state to allow a two-dimensional floating of the jaws within the limits of the pivot pin play. An additional pull-wire can be used to close the housing sides into the locked state. While FIG. 9 is shown as a grasper, scissors are also possible to use with this embodiment. When tension on the cable equals the spring force, the jaw is able to "float" and align with a lumen it is being advance through.

In many of the above embodiments, only a single jaw is depicted for ease of illustration. However, it is contemplated that in each of these embodiments opposing jaws may be utilized that transverse the lumen in parallel together, are then locked, and can be opened and closed through a flexible rod similar to the use of conventional laparoscopic instruments.

Other aspects of devices constructed in accordance with aspects of the present invention include the ability to incorporate multiple tools into the end effectors described above while still allowing for maneuvering through a curved lumen. As described herein, various configurations may be used to further streamline the end effector tool while incorporating additional functionality into the overall device.

Figure 10:
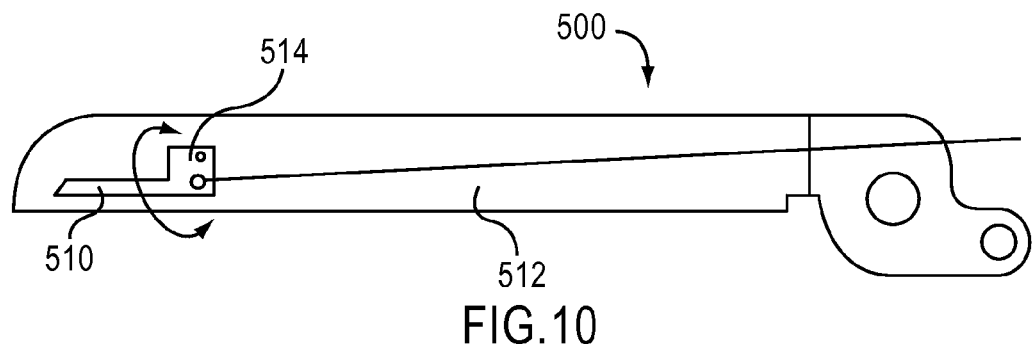
FIG. 10 shows an embodiment of a flip up end effector in accordance with aspects of the present invention.

With reference to FIG. 10, a scissor or tooth tool that can be raised/lowered on demand by the user is shown incorporated in an end effector. An end effector surface 500 includes a retractable tool such as a scissor blade 510 that can be deployed and/or retracted via actuation wire 512. This "flip-up" scissor may also be implemented in any of the multiple-tool embodiments described above. In addition, currently known tools may incorporate this tool design such as the Ligasure™ bipolar ligation device. In this example, the two opposing jaws act like graspers while a cutting element is adapted to emerge between the grasper to cut the coagulated/sealed vessel or tubular structure. In one example, the cutting tool is a straight "razor" blade that slides between the clamping jaws when activated by an external lever near the handle.

Similar to the description above, aspects of the present invention can relate to combine two instruments together within a fixed diameter. Two such combinable instruments may be a Maryland jaw and a scissor. A second instrument may be a bipolar clamping device. In one embodiment, the "blade" position of the scissor may be made to slide into a channel cut into the Maryland jaw. As described previously, in order to manipulate the elements in the jaws or blades of a scissor, an operator may move a lever or rotate a knob similar to currently marketed devices such as the lever on the Ligasure or the Lina Biploar that in both cases moves the cutting blade forward.

In accordance with another aspect of devices constructed according to the present invention, the structure of the device is hollowed or otherwise adapted to provide room for additional elements to actuate within the jaw. In one configuration, the top side of the top jaw is hollowed out, creating a hollow pocket section. The hollowing of the jaw can be achieved by drilling, milling, EDM, or other known methods. The shape of the hollow pocket section may depend on the function of an effect element, such as a cutting instrument, that will utilize the hollow section of the jaw.

Figure 11:
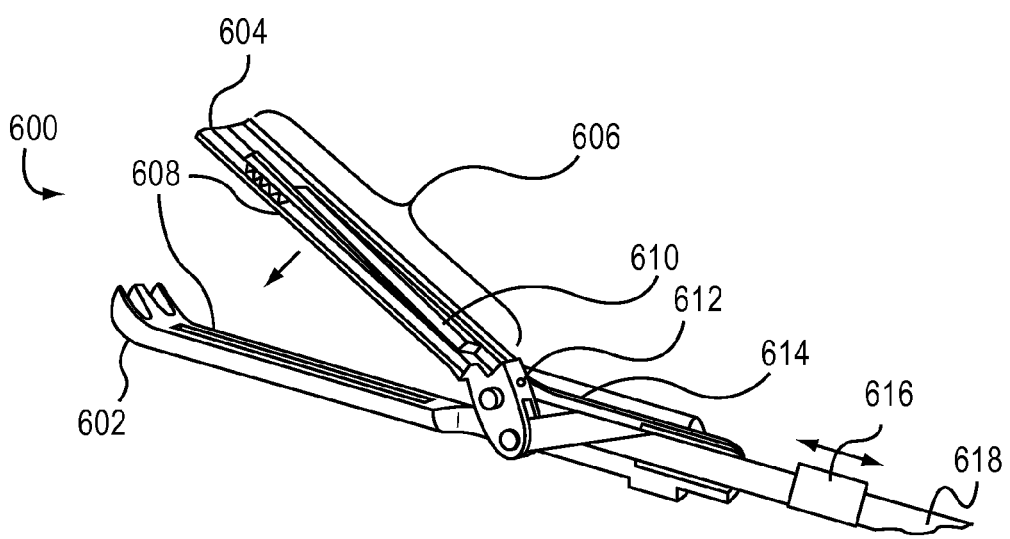
FIGS. 11 and 12 show an embodiment of a multi-function end effector in accordance with aspects of the present invention.
Figure 12:
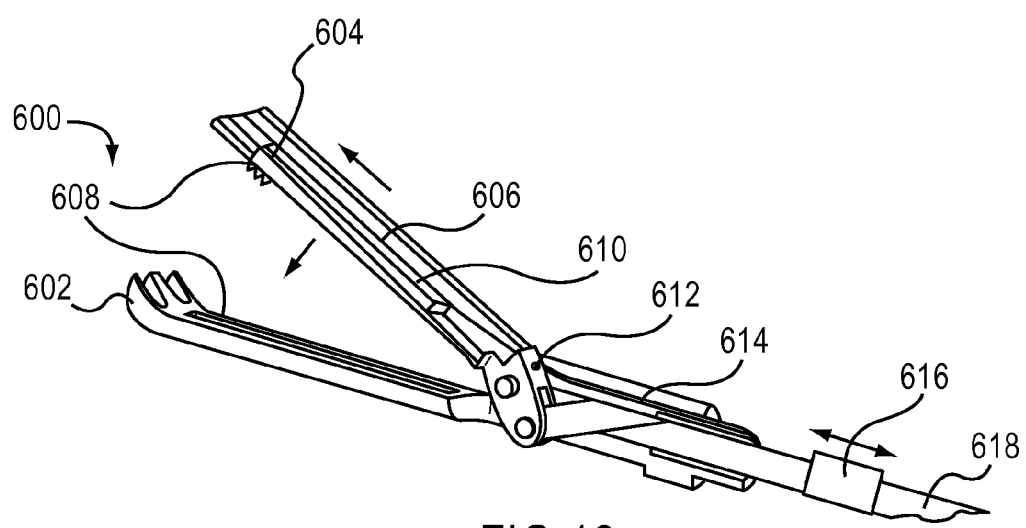

Another embodiment of a multifunction end effector instrument having a hollowed pocket section may include an actuator wire. The actuator wire can be a stiff wire which runs along a side the main rod. The wire may enter the hollowed pocket section from the main rod through a hole drilled into a back of the jaw. A distal end of the wire distal may couple to an actuation plate in the hollow section. A proximal end of the wire may couple to an operator actuation feature such as a lever, knob or handle. When the operator or surgeon moves the actuation member at the wire proximal end, the stiff wire translates the motion into displacement at the distal end, thereby moving the actuation plate distally. The wire may then return the plate to the original position when the actuation member is displaced in a return direction, with one return direction being a generally opposite direction of the initial actuation direction. FIGS. 11 and 12 show a representative example of a hollowed grasper jaw apparatus 600 that is adapted to include an additional element.

In FIGS. 11 and 12, a tool such as an end effector 600 includes opposing sections 602 and 604. The sections 602 and 604 are at least partially hollow such that a secondary effect element 608 can be recessed within the structure. An actuation plate 610 is disposed within the structure of the sections 602 and 604 and is adapted to slide or otherwise move along the length of the sections 602 and 604 such that when it is pushed toward the distal end of the end effector 600 it biases the effect element out of the sections 602 and 604 so that the effect element is exposed and operable. A hole 612 is disposed within the structure of the end effector 600 such that an actuation element, e.g. a wire 614, can pass through to the proximal end of the device where a user can control the action of the actuation plate 610 and the effect element 608. FIG. 11 shows the device with the effect element 608 in a retracted position while FIG. 12 shows the device with the effect element 608 in an extended position.

In one embodiment, the mechanical movement of the actuation plate 610 may be translated into another motion. For example, the actuation plate 610 may comprise a wedge-shaped cross-section with a bottom surface laying against the top surface of the effect element 608. The effect element 608 may also have a wedge-shaped cross-section to further emphasize the movement of the effect element 608. As the actuation plate 610 moves towards a distal end of the top jaw, the effect element moves towards a secondary position proximal an interior side of the top jaw. The movement of the effect element towards the interior side of the top jaw may also occur through the interaction of the actuation plate 610 and/or cams that are engaged with the actuation plate. FIG. 11 shows the device with the actuation plate 610 in a retracted position that allows the effect element 608 to remain within the body of hollow section 606. FIG. 12 shows the device with the actuation plate 610 in an extended position allowing the effect element 608 to protrude from the hollow section 606.

By moving the effect element 608 into its second and extended position, the function of the instrument in this particular embodiment changes from a grasper having anti-traumatic jaws such as, but not limited to, smooth jaws and/or tooth-less jaws, to an instrument with jaws that include more aggressive teeth. Moreover, this may be done without exchanging an instrument. As seen in FIGS. 11 and 12, an actuation tube 616 is shown as substantially encircling a portion of a main rod 618. The actuation tube 616 can be a tube section that surrounds at least a section of the main rod 618, moving independently from the main rod, and extending proximally to the handle area where an actuation member attaches to the actuation tube, the actuation member providing a movement interface with the surgeon. The actuation tube 616 can be a full tube, partial tube, multiple concentric tubes (each capable of driving an independent actuation plate) or a series of rods that all run parallel to the main rod 618.

Figure 13:
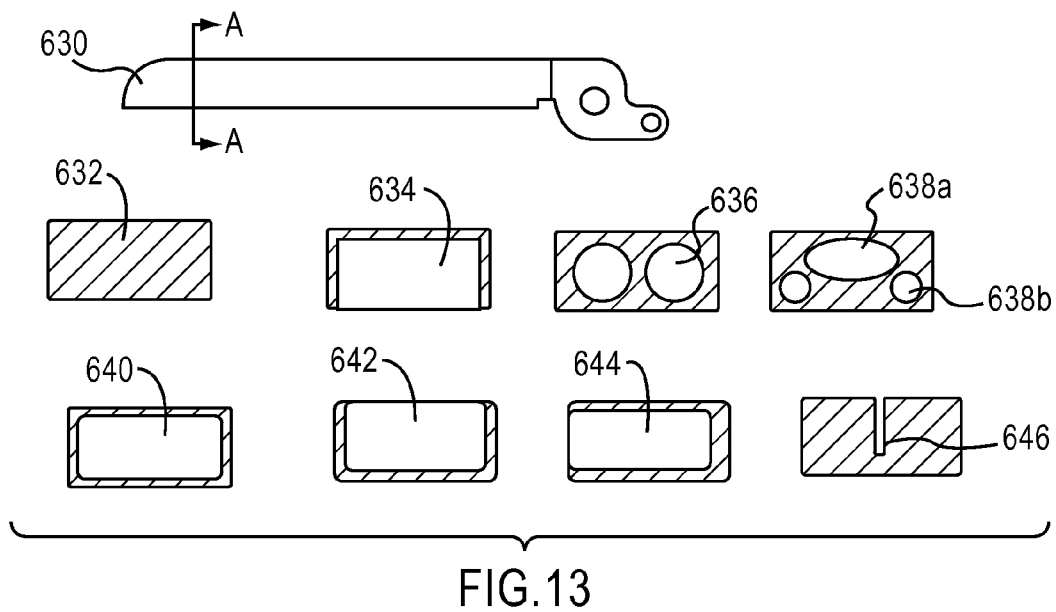
FIGS. 13 and 14 show various embodiments of hollowed end effector structures in accordance with aspects of the present invention.
Figure 14:
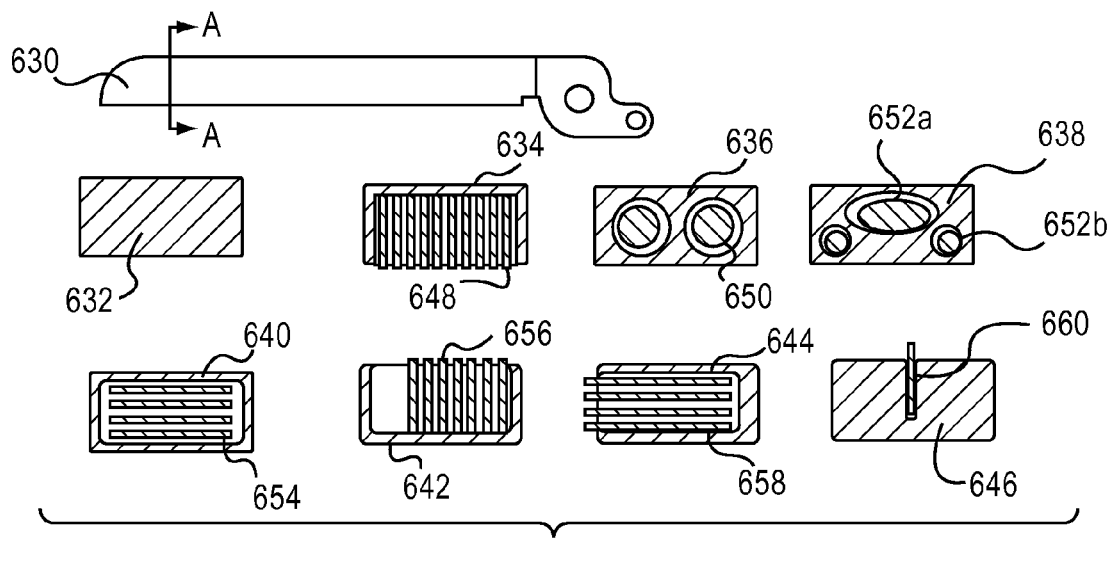

The hollowed jaw pocket section 606 can take on many shapes and forms depending on the application or effect desired from the end effector and required motion. For example, and as briefly described above, the hollowed jaw, or section of the jaw, may comprise a portion of the jaw being hollowed out for storage, concealment or use by end effectors to enable secondary motions and mechanisms. FIG. 13 gives representative examples of a typical jaw and a cross-sectional view of various hollowed pocket sections along section A-A. A longitudinal cross section of end effector is shown in FIG. 13 as 630. End effector 630 is intended to represent a generalized tool or end effector and is not meant to limit the disclosure to any particular embodiment. FIGS. 13 and 14 are meant to be representative of many different types of surgical tools and end effectors. Reference numbers 632-646 show various embodiments of section A-A from end effector 630 and the various shapes that a hollowed portion of that end effector may take. For example, reference number 632 refers to a typical solid body end effector 632 with no hollowed portion. Reference number 634 refers to a hollowed rectangular portion within the cross section of the end effector 630. Reference number 636 refers to one or more hollowed circular portions within the cross section of the end effector 630. Reference numbers 638a and 638b refer to one or more oval and/or circular hollowed portions within the cross section of the end effector 630. Reference numbers 640, 642, 644 and 646 each refer to various other shapes and configurations of a hollowed portion within the cross section of the end effector 630.

The hollowed portions of the end effector or jaw section may be adapted to receive one or more end effectors tools. For example, FIG. 14 shows the same example jaw sections as shown in FIG. 13 with example end effectors, effector plates, or actuation plates in the hollowed out sections. As shown in FIG. 14, the effectors that are recessed within the hollowed portions of the jaw section 630 can be almost any shape style and size to match the shape of the hollowed section. The shapes may be designed based on the desired operation or motion. For example, the effectors can be formatted as a series of parallel plates 648 that can act independently or together slide into and out of the jaw. The effectors can also be shaped as oval or circular tubes 650, 652a and 652b to align with the similarly shaped hollowed portions. The effectors can be sized and oriented in many different ways such as shown by reference numbers 654, 656, 658 and 660.

Figures 15A, 15B:
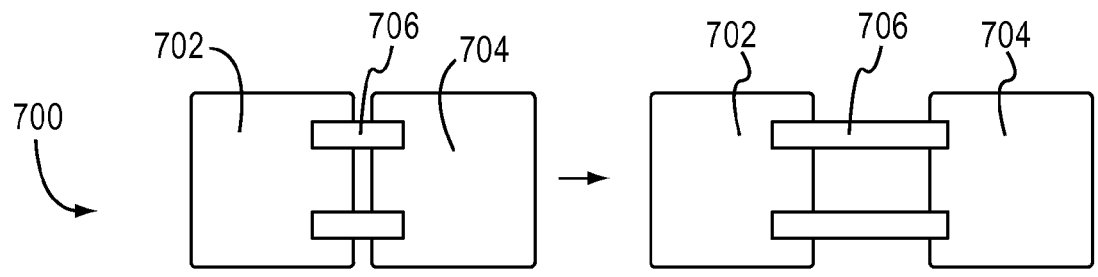
Figure 16A:
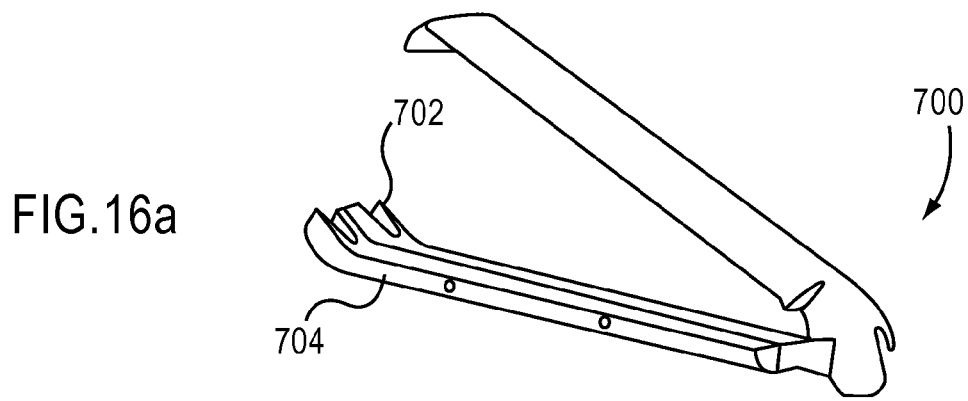
Figure 16B:
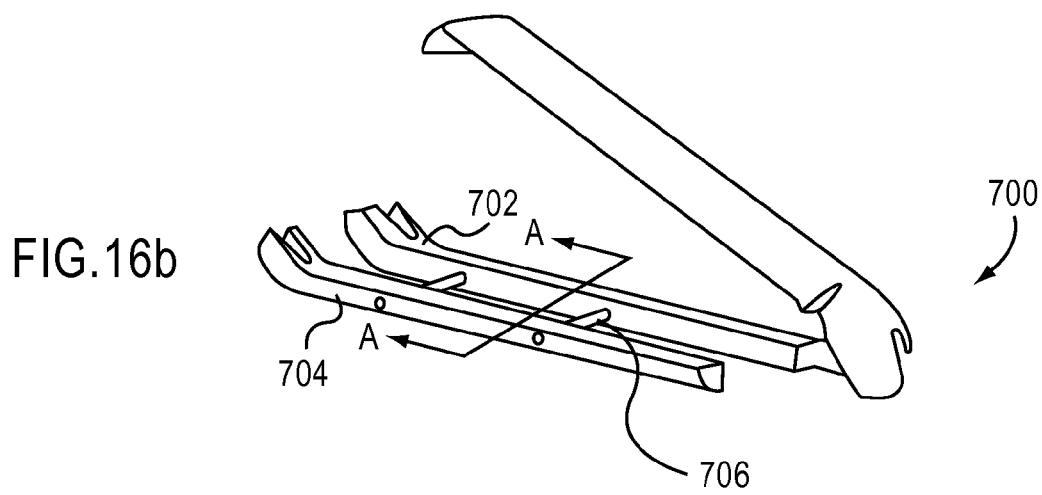

Another aspect of a multifunctional end effector may provide a jaw assembly that can transition from a smaller narrower assembly into a larger/wider mechanism by utilizing effect plates or similar mechanisms to selectively separate the jaw portions into a twin jaw arrangement. In this embodiment, a surgeon can operatively slide the two portions of the jaws together to create a smaller device profile when needed to retract the tool through a cannula or other lumen and expand the jaws when needed to perform a surgical procedure. In one embodiment, one of the upper jaw and lower jaw, or both the upper jaw and lower jaw may comprise this twin jaw format. One or both of the upper jaw and lower jaw may also comprise one or more additional end effectors as described previously. The movement of the jaws (together, apart) can be achieved by using similar actuation wires, plates or tubes through hollow areas in the jaws to achieve the desired motion of moving the jaws together or apart. Again, one of the two motions (push jaws apart or pull jaws together) can be replaced with a spring bias to replace one of the two motions that is performed by an actuation wire. FIGS. 15 and 16 show a representative example of a twin jaw end effector 700 as described above. FIG. 15 is a representative cross section along section A-A in FIG. 16. End effector 700 includes two sections 702 and 704 joined by sliding mechanism 706 that allows the sections 702 and 704 to separate and selectively adjust the distance between the sections 702 and 704. FIG. 15A shows the jaw sections in a narrowed configuration and FIG. 15B shows the jaw sections in a widened configuration. FIGS. 16A and 16B show a perspective view of the end effector 700 in its narrowed (FIG. 16A) and widened (FIG. 16B) configurations.

Since space is an important consideration in many of the enhanced control devices using multifunctional end effectors as described herein, actuation wires may be required to perform various functions. For example, it may be necessary for a single wire to perform the scissor opening and closing. Therefore, in one embodiment, the actuation wire may be required to "push" the scissor open. Depending on the end effector and desired end effector functionality, pushing on an actuation wire may induce movement in the wire similar to pushing on a rope. Therefore, the wire may be unable to transmit sufficiently large forces since the wire may buckle and twist. However, in the scissor closing operation, as well as other end effector operations, the wire can work and apply sufficient force to close the scissor. To aid in opening the scissor, the scissor blades can be designed with springs to bias the scissors open. The springs can either aid the wire in pushing the blades open or replace the need for pushing the wire. The spring can be a wound torsional spring located near the scissor pivot or a leaf spring that flexes when the scissors are closed.

In accordance with another aspect, a multifunctional end effector tool may be adapted as a grasper/scissor combination. In general, an instrument in accordance with this aspect has the ability to both act as a grasper/dissector and the ability to cut tissue by engaging/disengaging certain aspects of the tool. In this sense, a laparoscopic instrument has the ability to perform multiple functions without having to remove the instrument from the patient.

In accordance with one aspect the grasper jaws are formatted to be narrower than usual, for example, they may be half as wide as conventional instruments. One or both of the jaws are able to slide to the side, so that it does not come down and contact the other jaw for grasping. In this position, the jaws create shear between their edges rather than force between the jaw surfaces, thus creating a cutting action rather than a grasping action. Because the jaws have a narrower profile, one of the jaws can then be slid over the top of the other so that the jaw surfaces will engage each other (as opposed to the jaw edges) and thus create a grasping action.

Figure 17A:
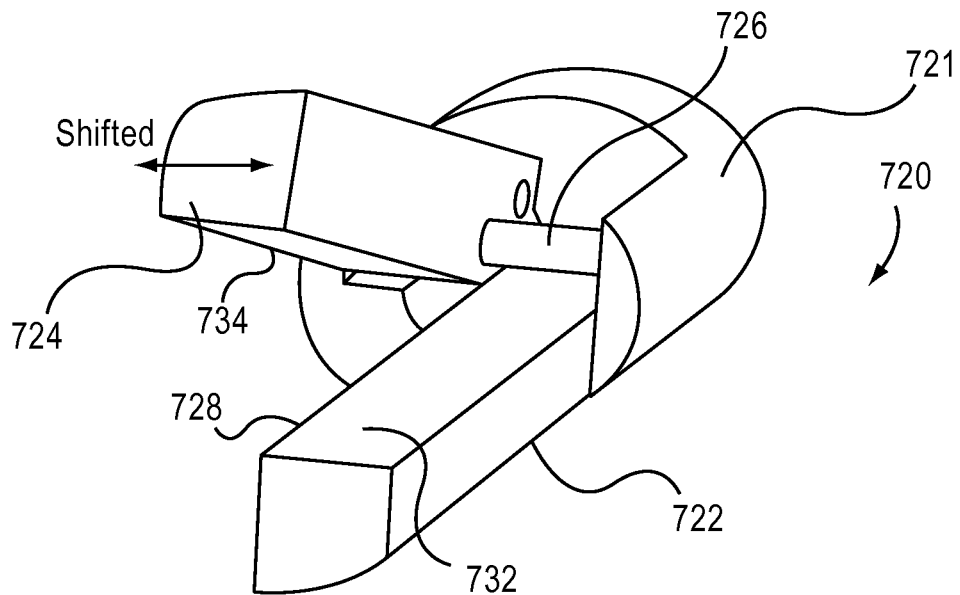
FIGS. 17A and 17B show another embodiment of a sliding jaw end effector in accordance with aspects of the present invention.
Figure 17B:
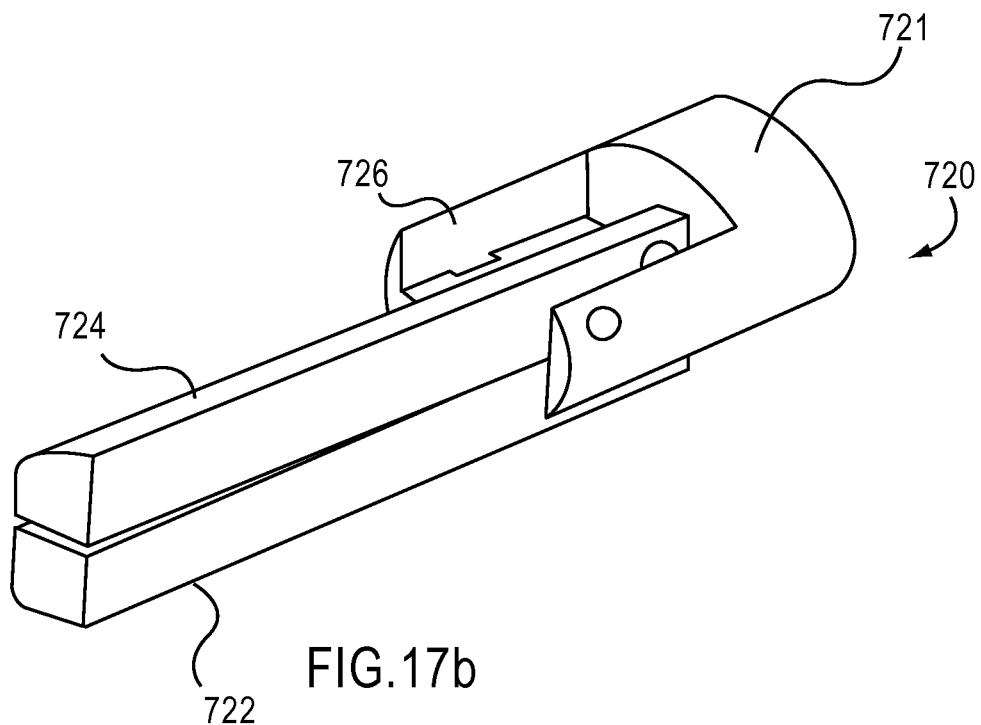

FIGS. 17A and 17B show an example of this embodiment. Referring to FIG. 17A an end effector 720 includes a housing 721 that serves to mount a pair of end effector sections 722 and 724. Each of the sections 722 and 724 are mounted on a pin 726 that allows the sections 722 and 724 to both pivot up and down as well as slide along the length of the pin 726. Section 722 includes a cutting edge 728 and a grasping surface 732 and section 724 includes a cutting edge 730 and grasping surface 734. The configuration of the end effector sections 722 and 724 on the pin 726 allows the sections to function together as a cutting tool in a first position (FIG. 17A) and also as a grasping tool in a second position (FIG. 17B) depending on the position of the respective sections 722 and 724.

Figure 18A:
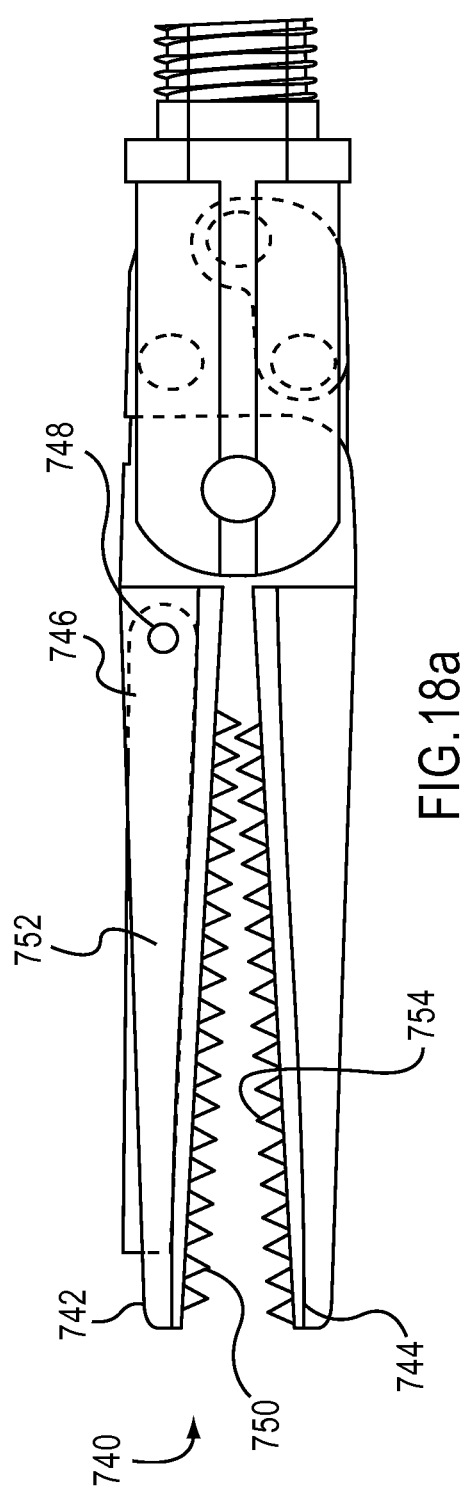
FIGS. 18A and 18B show an embodiment of a flip-up scissor design in accordance with aspects of the present invention.
Figure 18B:
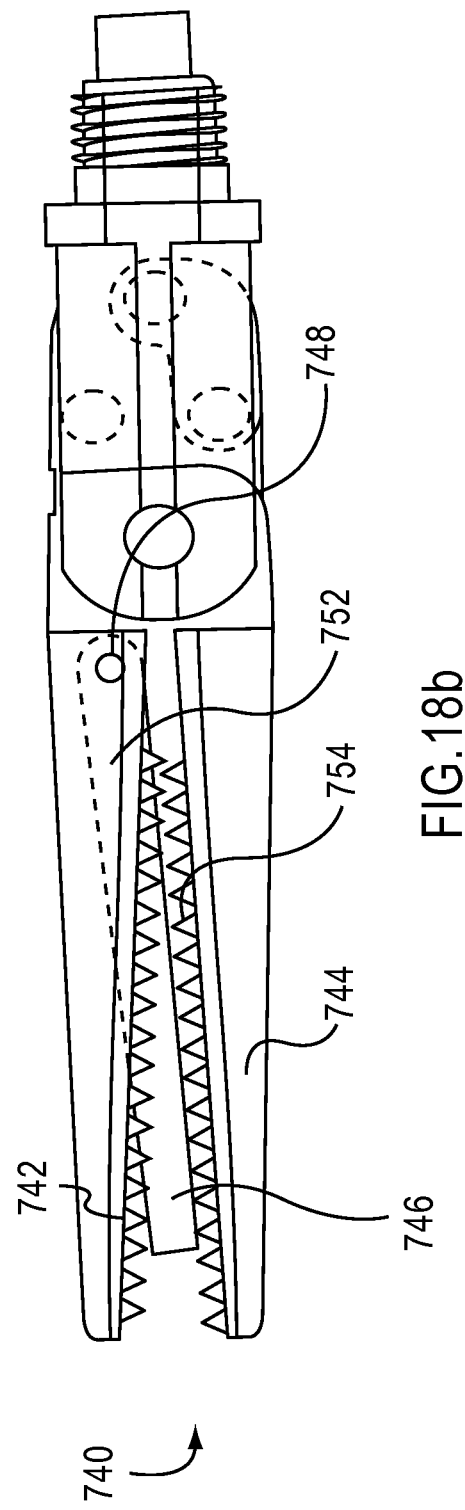

In accordance with another aspect, a blade (or blades) may be stored on the edge of the grasper jaws. The blade is stored out of the way when grasping/dissecting is the intended motion. When the user wants to have a cutting action, the blades "pop out" or into position so that they interact with each other, or with the edge of the opposite jaw to create a shear cutting action. FIGS. 18A and 18B show an example of this embodiment where an end effector 740 includes jaw sections 742 and 744, each including grasping surfaces 750 and 754 respectively. A cutting blade 746 is rotatably mounted along side one the jaw sections by a pin, hinge or similar structure 748 and includes a cutting surface 752 that is adapted to engage with an edge of the opposing jaw surface in order to perform a cutting function when engaged by a user. When not being used, the cutting blade 746 can be stored out of the way of the grasping surfaces alongside one of the grasper jaws 742 or 744. A single cutting blade can be utilized as shown in FIGS. 18A and 18B or two cutting surfaces can be provided, one disposed along each of the grasper jaws 742 and 744.

The blade(s) may be stored up & out of the way when not in use (as shown in FIGS. 18A and 18B) or could be stored inside the jaw as described with the hollowed jaw embodiments of FIGS. 13 and 14. Shear forces are created by the blade hitting the outside of the other jaw (or other blade) when in the "engaged" position. The rest of the time, the blades do not interact with any part of the jaws because they are stored out of the way.

Figure 19A:
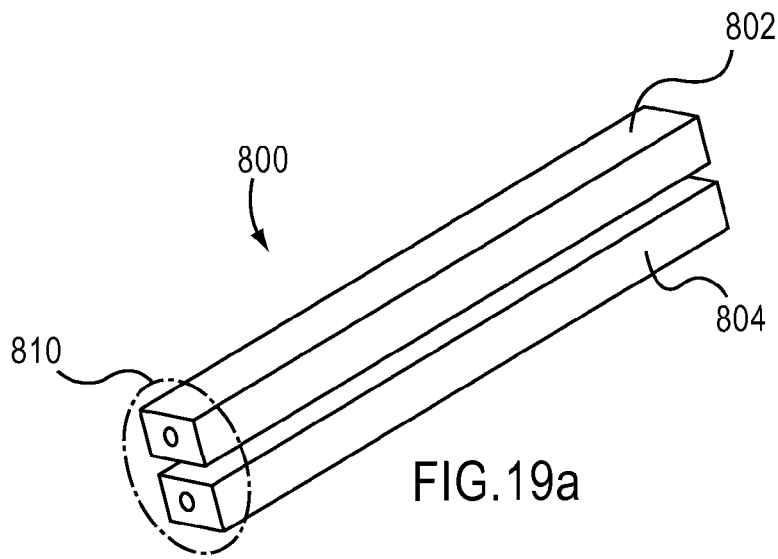
FIGS. 19A-19C show an embodiment of a rotatable end effector in accordance with aspects of the present invention.
Figure 19B:
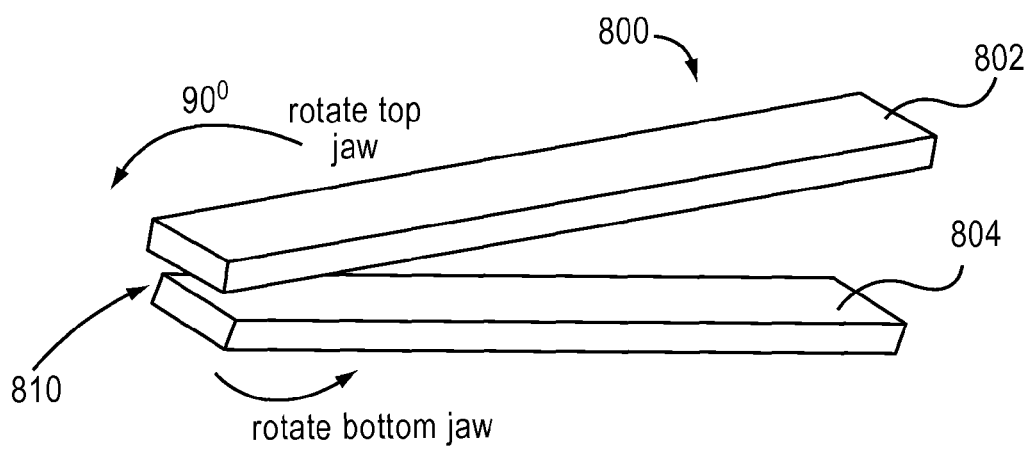
Figure 19C:
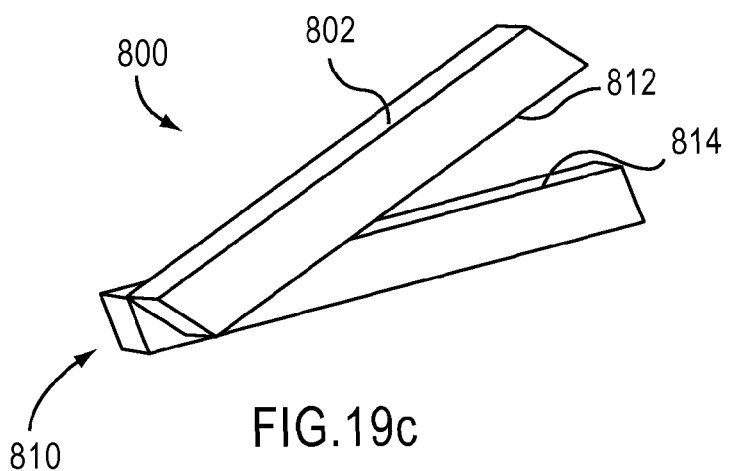

In accordance with another aspect, the jaws of a grasper or other end effector include a multi-directional joint capable of rotation about more than one axis. For example, jaws joined in this manner are capable of pivoting to create a grasping motion and can also rotate approximately 90 degrees to form a cutting device with the edges of the jaw surfaces. The jaw can thus transform from a pair of larger flat areas to a pair of opposing cutting surfaces. FIGS. 19A-19C illustrate a generalized drawing of a device 800 capable of functioning as a both a grasper and cutting tool. Device 800 includes opposing jaw sections 802 and 804 connected by a multi-directional hinge 810. In this embodiment, the hinge points are offset from each other with relation to the centerline of the jaw surface 802 and 804. In FIGS. 19A and 19B the jaws 802 and 804 are parallel for a grasping/dissecting function. In FIG. 19C the jaws 802 and 804 are shown rotating about a first axis so that they are now rotated and locked into a scissor position, allowing sheer interaction between the edges 812 and 814 of the jaw sections 802 and 804 for cutting.

In another embodiment, the jaw sections are formed to be relatively thin at the tip are tapered along their length (making the base wider than the tip) in order that the deflection of the jaw sections (e.g. the blades of the scissor function) can be counteracted while keeping the tip relatively thin (as the width of the blades close to the point of contact is not as critical). Having the blades thicker at the base leads to a stiffer, stronger blade. This thickness aids the stiffness less and less as moving towards the tip. Thus, by tapering the blades a strong, thin scissor can be created.

In accordance with another aspect of a device constructed in accordance with the present invention, a multi-functional end effector is disclosed in which an existing FTE (Fixed Tip Electrode) product is modified to include a cutting device such as a scissor. For example, an "L" hook FTE device currently manufactured by Encision may be modified to include a scissor and actuation device. Unmodified, the "L" hook comprises a metal "L" electrode extending from an insulation layer, the electrode being adapted to provide a dual use of passing through and pulling back tissue while producing electrosurgery effects. Coupling an additional metal device such as a single scissor blade to the electrode with a hinge-like structure provides a surgeon the additional ability to perform cutting.

Figure 20:
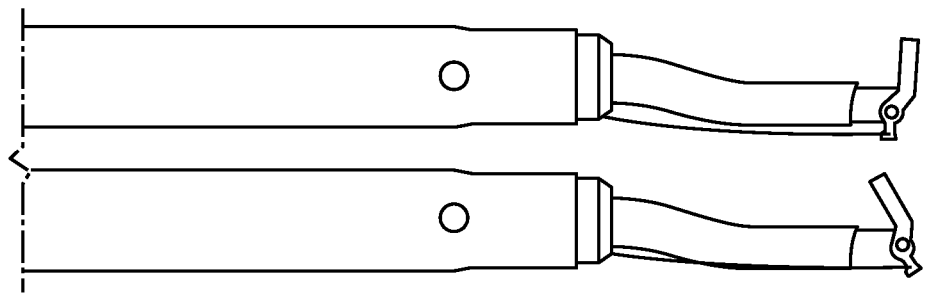
FIGS. 20 and 21 show various embodiments of a multi-functional end effector device in accordance with aspects of the present invention.

One scissor embodiment may be actuated by a separate lever near the handle of the FTE. The lever may couple to an actuation wire end, which has a second end coupled to the hingedly coupled scissor blade. The wire may be adapted to open or and/or close the blade through pushing and/or pulling the wire with the lever. A spring may also be coupled to the wire and/or the blade to close and/or open the blade. The surgeon would use the instrument with the scissor in a closed position thus making the "L" hook still perform and generally shaped like the current "L" hook device. When needed, the surgeon can activate the actuation wire and open/close the scissor to perform cutting. A version of this embodiment may utilize a side of the "L" hook to hingedly extend and be used as the scissor blade cutting surface. This same principle can be applied to other tip shapes in Encision's catalog for FTE (s), SIE(s) and for graspers/dissectors. FIG. 20 gives a representative example of such a design.

Figure 21:
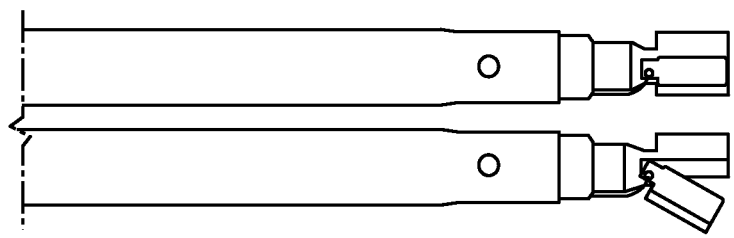

One variation on the scissor embodiment comprises a FTE where the tip itself is the scissor. In this embodiment, a FTE spatula tip is used. A spatula tip typically comprises a flat square shape for electrosurgical use. In the modification, the tip is comprised of two separate surfaces, with one of the surfaces comprising a scissor surface. When the two surfaces are aligned in parallel, the surfaces generally resemble the original spatula tip shape. One of the surfaces is then adapted to operate similar to the previous variation wherein the surgeon can activate an actuator wire to open the scissor surface by manipulating a lever from one position to another position. The lever may comprise a handle, a twistable knob, or sliding a plate. In one embodiment, the motion of these components provide linear displacement of the actuator wire to operate the scissor function. FIG. 21 gives a representative example of this design.

Figure 22:
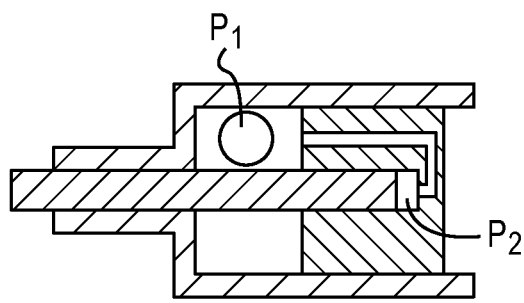
FIG. 22 shows an embodiment of a device for transferring force and/or motion to an end effector.

FIG. 22 shows a representative example of a system that aids in the transmission of force, motion and or power to the distal end of a surgical tool, such as an end effector or other functional device. Even though modern generation end effector devices have a smaller footprint, it is still desirable to enable the device to impart a larger force on the tissue being operated on. An apparatus like that described in FIG. 22 may be incorporated into an end effector so that forces applied by the user or surgeon may be effectively transmitted to the tool. Both hydraulic and air assisted devices are contemplated in such systems.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A surgical tool adapted to transverse through a curved passageway, comprising:
   a semi-rigid elongated member;
   a plurality of segmented body sections disposed along the length of the semi-rigid elongated member;
   a first control wire flexibly engaged along a first outer surface portion of the plurality of body sections, the plurality of body sections fixedly disposed along a length of the first control wire,
   a second control wire flexibly engaged along a second outer surface portion of the plurality of body sections, the plurality of body sections fixedly disposed along a length of the second control wire, wherein the first and second control wires are adapted to steer a distal end of the surgical tool and allow the plurality of body sections to move from a first fixed position to a second movable position;
   an actuator for steering the distal end of the surgical tool and enabling the first and second control wires to move the plurality of body sections from the first fixed position to the second movable position;
   wherein when the plurality of body sections are in the second moveable position the surgical tool is adapted to move through a curved lumen; and
   wherein when the plurality of body sections are in the first fixed position, the surgical tool is adapted to perform a surgical procedure.

2. The surgical tool of claim 1, wherein each of the segmented body sections comprises a portion of a tool surface and wherein when the plurality of segmented body sections are in the first fixed position, the segmented body sections form a unitary tool surface for performing a surgical procedure.

3. The surgical tool of claim 1 wherein the plurality of segmented body sections each have a substantially similar shape.

4. The surgical tool of claim 1, wherein the plurality of segmented body sections form a tapered device when in the first fixed position.

5. The surgical tool of claim 1 wherein the surgical tool comprises two opposing surfaces and wherein each of the opposing surfaces includes first and second body portions and a releasable connector joining the first and second body sections, wherein each connector is operable to reversibly engage each of the first and second end effector body sections in a first fixed position and in a second movable position.

6. The surgical tool of claim 1, wherein the surgical tool is a grasper.

7. The surgical tool of claim 1, wherein the elongated member is made from Nitinol.

8. The surgical tool of claim 1, further comprising an end effector engaged with the distal end of the elongated member.

9. The surgical tool of claim 8, wherein the end effector is a grasper.

10. A surgical tool adapted to transverse an end effector through a curved passageway, comprising:
    a semi-rigid elongated member;
    a plurality of segmented body sections disposed along the length of the semi-rigid elongated member;
    a first control wire flexibly engaged along a first outer surface portion of the plurality of body sections, the plurality of body sections fixedly disposed along a length of the first control wire,
    a second control wire flexibly engaged along a second outer surface portion of the plurality of body sections, the plurality of body sections fixedly disposed along a length of the second control wire, wherein the first and second control wires are adapted to steer the end effector and allow the plurality of body sections to move from a first fixed position to a second movable position;
    an actuator for steering the end effector and enabling the first and second control wires to move the plurality of body sections from the first fixed position to the second movable position;
    wherein when the plurality of body sections are in the second moveable position the end effector is adapted to move through a curved lumen; and
    wherein when the plurality of body sections are in the first fixed position, the end effector is adapted to perform a surgical procedure.

11. The surgical tool of claim 10, wherein the end effector is a grasper.

* * * * *